(12) United States Patent
Carter

(10) Patent No.: US 11,197,808 B2
(45) Date of Patent: Dec. 14, 2021

(54) LIQUID FORMULATION FOR TREATING PLANTS AND SKIN AND METHOD OF USE

(71) Applicant: Seriously Clean, Ltd., Nixa, MO (US)

(72) Inventor: Milo Carter, Ozark, MO (US)

(73) Assignee: Seriously Clean, Ltd., Nixa, MO (US)

( * ) Notice: Subject to any disclaimer, the term of this patent is extended or adjusted under 35 U.S.C. 154(b) by 0 days.

(21) Appl. No.: 16/452,623

(22) Filed: Jun. 26, 2019

(65) Prior Publication Data
US 2019/0388311 A1 Dec. 26, 2019

Related U.S. Application Data

(60) Provisional application No. 62/689,878, filed on Jun. 26, 2018.

(51) Int. Cl.
*A61K 8/22* (2006.01)
*A61K 8/25* (2006.01)
*A61Q 19/10* (2006.01)
*A61K 8/96* (2006.01)

(52) U.S. Cl.
CPC .......... *A61K 8/22* (2013.01); *A61K 8/25* (2013.01); *A61K 8/965* (2013.01); *A61Q 19/10* (2013.01)

(58) Field of Classification Search
CPC ....... C11D 3/1246; C11D 3/48; C11D 3/3956; C11D 3/1266; C11D 3/128; A61Q 19/10; A61Q 19/00; A61K 8/0212; A61K 8/25; A61K 8/22; A61K 8/965; A01N 59/00; A01N 25/08
See application file for complete search history.

(56) References Cited

U.S. PATENT DOCUMENTS

| | | | |
|---|---|---|---|
| 9,381,214 B2 * | 7/2016 | Sampson | B65D 65/38 |
| 2002/0072288 A1 * | 6/2002 | Hei | C11D 3/48 442/59 |
| 2008/0214396 A1 * | 9/2008 | Best | A01N 25/12 504/101 |
| 2008/0234328 A1 * | 9/2008 | Schlatter | A01N 47/40 514/341 |
| 2015/0368269 A1 * | 12/2015 | Smith | C07D 413/06 514/223.2 |
| 2015/0369019 A1 * | 12/2015 | Raffn | E21B 33/138 166/278 |
| 2017/0355799 A1 * | 12/2017 | Veiseh | A61K 35/12 |

* cited by examiner

*Primary Examiner* — Blessing M Fubara
(74) *Attorney, Agent, or Firm* — Clark & Brody LP

(57) ABSTRACT

An aqueous formulation for treating insects and fungal diseases on plants includes effective amounts of an HOCl-containing electrolyzed oxygenated aqueous solution, one or both of a food grade diatomaceous earth and a clinoptilolite zeolite, and one or more of a sodium magnesium fluorosilicate and a bentonite clay. The formulation, which is non-toxic to humans and pets, can be sprayed on the plants to kill insects and fungi and has a long dwell time to improve the effectiveness of the components of the formulation against insects and fungi. In particular, the formulation will kill bacteria, virus, mold, fungi, and may be used on food crops. The formulation also may be used as a plant and foliar cleaner and/or the formulation can be used to treat skin of a person to improve skin health.

13 Claims, No Drawings

LIQUID FORMULATION FOR TREATING PLANTS AND SKIN AND METHOD OF USE

FIELD OF THE INVENTION

The invention relates to a liquid formulation designed to treat/cleanse plants as an insecticide/fungicide, to clean plants, and to treat/cleanse the skin of a person as a beauty aid.

BACKGROUND ART

There are a number of different formulations designed to treat/cleanse plants for insect and fungi control. These formulations can be problematic in that some require personal protection equipment, some can cause skin and bronchial irritation, and some can be harmful if ingested.

There are also a number of organic and less toxic formulations in the prior art. However, many of these formulations can leave an undesired residue on the plants being treated.

There are also a number of different formulations designed to treat/cleanse human skin for beautification purposes.

As such, a need exists for improved formulations for treating/cleansing plants that are in need of fungus and insect control and human skin for beautification purposes.

SUMMARY OF THE INVENTION

One object of the invention is to provide a liquid formulation that is designed to kill insects and fungi on plants and act as a plant cleaner or plant wash.

As a plant cleaner the invention will remove dirt and debris from the surface of the plant's leaves, stem and stalk. The pores of the leaf (Stomata) are a major element in a plant's respiration. Obstruction of the stomata and thereby the obstruction of respiration will lead to less the optimal plant health and in a worst case scenario death by suffocation. It is the intention of the invention to improve the overall health and vigor of a plant by maximizing the respiratory capacity of the stomata and thereby maximizing the plant's potential.

Another object of the invention is to provide a liquid formulation that is designed to treat skin for beautification and health purposes. One way of improving the condition and appearance of skin is to deep clean the pores. The invention, to this end, acts as a facial mask. The clays in the liquid formula behave in a manner that is known to one skilled in the art to form a facial mask absorbing excess sebum and clearing the pores. The hypochlorous acid, as it has been demonstrated, in various wound formulas acts as a germicide, killing bacteria that would inflame or infect the pores of the user. Hypochlorous acid has been shown to be effective against the various bacteria and situations associated with acne vulgaris, oily skin and other skin related symptoms. The gentle pH of the product coupled with the oxidation of the bacteria and the absorption of excess sebum, leaves the skin smooth, clean with a polished appearance.

Other objects and advantages will become apparent as a description of the invention proceeds.

In satisfaction of the foregoing objects and advantages of the invention, an aqueous formulation for treatment of one or more of insects and fungi on plants and skin of a person, as well as being used as a plant wash is provided. The formulation comprises, in weight percent:

about 0.5 to about 5.0% of one or both of sodium magnesium fluorosilicate (nano) and a bentonite clay;

about 0.5 to about 10.0% of one or both of a food grade diatomaceous earth and a clinoptilolite zeolite; and the balance a HOCl-containing electrolyzed oxygenated aqueous solution having a FAC of 16 to 500 ppm.

Preferably, the aqueous formulation has about 0.75 to about 2.0% of the one or both of the sodium magnesium fluorosilicate (nano) and the bentonite clay and about 0.75 to about 5.0% of one or both of the food grade diatomaceous earth and the clinoptilolite zeolite. More preferably, the aqueous formulation has about 1.0% of the one or both of the sodium magnesium fluorosilicate (nano) and the bentonite clay and about 1.0% of one or both of the food grade diatomaceous earth and the clinoptilolite zeolite. The FAC of the HOCl-containing electrolyzed oxygenated aqueous solution can range between 30 and 300 ppm.

In one embodiment, the aqueous formulation can include both the diatomaceous earth and the clinoptilolite zeolite. In this embodiment, the ratio of diatomaceous earth to clinoptilolite zeolite ranges from 1:1 to 1:30, with a preferred ratio being about equal parts diatomaceous earth to clinoptilolite zeolite.

In another embodiment, the aqueous formulation can contain either diatomaceous earth or clinoptilolite zeolite.

Another aspect of the invention is the use of the inventive aqueous formulation. One use is to treat one or more plants for insect and fungal disease control by applying an effective amount of the aqueous formulation to the one or more plants to kill at least insects and fungi on the one or more plants.

Another aspect of the use of the aqueous formulation is for skin treatment or cleansing. Here, a person's skin is treated by applying an effective amount of the aqueous formulation of claim 1 to the person's skin to improve skin health and cleanliness.

The formulation can also be used as a plant cleaner or plant wash to improve the plant health and vigor, particularly by removing dirt and debris from a surface of the plant, including leaves, stalks, stems, and the like.

In either insecticide/fungicide or skin treatment use, the aqueous formulation can include either the diatomaceous earth or clinoptilolite zeolite or a combination of both.

DETAILED DESCRIPTION OF THE INVENTION

The invention is a liquid formulation that contains effective amounts of diatomaceous earth, a sodium magnesium fluorosilicate or a bentonite clay or a combination of both, which is manufactured from naturally occurring inorganic mineral salts and is insoluble in water but hydrates and swells to give colorless, translucent colloidal dispersions (available off the shelf as Laponite XL-21 XR (nano)), and an anolyte water, which is an electrolyzed oxygenated water containing an effective amount of stabilized hypochlorous acid (HOCl). This electrolyzed oxygenated aqueous solution is available off the shelf under the brand Nixall® and is referred hereinafter as a HOCl-containing electrolyzed oxygenated aqueous solution either produced from potassium chloride or sodium chloride.

The diatomaceous earth is of food grade quality and is approved by the National Organic Program (NOP) and is readily available from commercial suppliers. It is also recognized by the USDA and EPA as a minimal risk substance and requires no EPA testing under FIFRA 24(b). 40 CFR 180.1017—Diatomaceous earth; exemption from the requirement of a tolerance.

The sodium magnesium fluorosilicate sold as Laponite XL-21 XR is a Food and Drug Administration (FDA) and Food, Drug, and Cosmetic (FD&C) Act approved material for use in toothpaste, cosmetics, and other skin applications. The XR designation indicates that the material has been sterilized with gamma irradiation. It is believed that the non-irradiated Laponite could also be used as part of the inventive formulation.

All ingredients in the HOCl-containing electrolyzed oxygenated aqueous solution are non-toxic and do not harm healthy tissue. One example of the makeup of the HOCl-containing electrolyzed oxygenated aqueous solution is electrolyzed oxygenated water ($H_2O$) (99.94%), sodium chloride (NaCl) (0.048%), hypochlorous acid (HOCl) (0.01%), and sodium hypochlorite ion (NaOCl) (0.002%).

The HOCl-containing electrolyzed oxygenated aqueous solution in its concentrated form typically contains about 0.046% HOCl with the balance being the electrolyzed oxygenated water and other ingredients. This results in a free available chlorine (FAC) of around 500 ppm. The HOCl-containing electrolyzed oxygenated aqueous solution can be used in a range of FAC of about 16 ppm (1/32 dilution) to 500 ppm and the HOCl-containing electrolyzed oxygenated aqueous solution would just be diluted to obtain the desired FAC value. Another preferred dilution would be about 30 ppm, which is a 1/16 dilution from the 500 ppm concentrated solution. The dilution is accomplished by adding distilled or deionized water to invention.

The HOCl-containing electrolyzed oxygenated aqueous solution is a relatively Non-toxic class IV disinfectant and is cleared by the EPA as such.

Lethal dose 50 (LD50) for all ingredients is not achievable through natural means.

From a weight percentage range standpoint, one embodiment of the formulation can be as follows:

0.5 to 5.0% of one or both of sodium magnesium fluorosilicate (nano) and a bentonite clay;

0.50 to 10.0% food grade diatomaceous earth; and the balance the HOCl-containing electrolyzed oxygenated aqueous solution having a FAC of 16 to 500 ppm.

More preferred ranges are 0.75 to 2.0% for the sodium magnesium fluorosilicate (nano) and/or bentonite clay; 0.75 to 5.0% food grade diatomaceous earth; and the balance the HOCl-containing electrolyzed oxygenated aqueous solution.

An even more preferred formulation would be about 1.0% for the sodium magnesium fluorosilicate (nano) and/or bentonite clay, about 1.0% food grade diatomaceous earth; and the balance the HOCl-containing electrolyzed oxygenated aqueous solution.

It should be understood that the sodium magnesium fluorosilicate is a preferred component of the formulation for its swelling and gel characteristics but bentonite clay is believed to work equally as well in terms of imparting the needed swelling and gel characteristics of the formulation. Bentonite is an absorbent aluminum phyllosilicate clay made up mostly of montmorillonite. There are different types of bentonite based on the respective dominant element in the material, e.g., potassium, sodium, calcium and aluminum, and any of these types of clays are believed to be suitable for use in the invention formulation, including natural ones and synthetics. It is believed that the same weight percentages would be used for these clay materials as used for the sodium magnesium fluorosilicate. Moreover, a combination of the bentonite and sodium magnesium fluorosilicate could be used as well.

The formulation in one use is intended for treating insects and fungi on plants. Examples of conditions of plants and pests on plants include powdery mildew and other fungi, botrytis, spider mites, whitely and similar pests. It is also believed that the formulation may also be effective against viruses and other microbial pathogens.

The formulation can be applied to the plants in any manner and preferred ways include manual spraying and electrostatic spraying. While the rate of application of the formulation can vary depending on the plants being treated, an example of an application would be to as follows. 16 gallons at a 30 ppm FAC would be expected to treat an acre of plants, which is about a gallon for 2700 square feet. Multiple applications can be made over a week's time and the concentration of the formulation can be varied as part of the multiple applications. For example, a formulation with a higher FAC content could be used for the initial application on a given area and then a more dilute formulation with a lower FAC content could be used in subsequent applications. Further yet, the formulations could be diluted a little in terms of FAC content for each subsequent application.

One problem in the prior art is that plants intended for human consumption are often sprayed/treated by chemicals that not only are poisonous to insects, fungi, and virus but are also poisonous to humans and pets. This problem is alleviated with the inventive formulation as the formulation is effective against plant pathogens but is non-toxic to humans and pets.

Another advantage of the invention is providing an increased dwell time for the formulation to act. An issue for spray applications of insecticide, fungicides, and the like is the dwell time of the material sprayed on the plant. Often times, the material runs off the plant before it can function in its intended use. The addition of sodium magnesium fluorosilicate allows the diatomaceous earth to adhere to the plant for a longer time that if just dusted on the plants. The presence of the sodium magnesium fluorosilicate also allows the HOCl-containing electrolyzed oxygenated aqueous solution to dwell longer on the plant as well by stopping dripping and run off.

The inventive formulation is multi-functional in terms of insects and fungi. That is, the HOCL-containing electrolyzed oxygenated aqueous solution challenges the microbial pest by oxidation of organelles and genetic material. Multicellular pests can be mechanically damaged by the diatomaceous earth and sodium magnesium fluorosilicate via suffocation, desiccation, and internal damage to the gut. The HOCl-containing electrolyzed oxygenated aqueous solution also interferes with the chemoreceptors used by some insects to locate food, thus making it difficult for the insect to find a plant to feed on.

While the formulation can be made in any manner, a preferred manner is as follows:

a) Hydrate the sodium magnesium fluorosilicate under high shear using the appropriate amount of filtered water.

b) Once the sodium magnesium fluorosilicate is hydrated, the HOCl-containing electrolyzed oxygenated aqueous solution and diatomaceous earth are added, and the mixture is again subject to high shear.

c) The final FAC can be adjusted by dilution once the formulation is finally mixed or the FAC can be adjusted prior to the hydration and mixing steps and the same concentration solution is used both for the hydration of the sodium magnesium fluorosilicate and the additional addition of the solution to obtain the desired weight percentages of the diatomaceous earth and sodium magnesium fluorosilicate.

The inventive formula can be used on any types of plants, including both indoor and outdoor plants, flowers, vegetables, food plants, tobacco ornamentals, trees, shrubs, and the like, that would be susceptible to damage from insects and fungal diseases. More preferred plants for application include *cannabis* and grapes, hops, oranges, indoor grown vegetables, and ornamental plants like Boston ferns and orchids. It should be understood that this listing is only exemplary and any plants in need of insect or fungal disease control would be candidates to receive one or more applications of the inventive formulation.

The inventive formulation may also be used as a plant wash, removing dirt and debris from foliage and stems and unwanted biofilm from the roots of hydroponic plants. The formulation can be applied in any manner to the plant surfaces to remove unwanted material from the surfaces, including spraying with sufficient pressure to remove the unwanted material, wiping or brushing or the like.

When using the formulation as a plant wash, the mode of application could vary depending on the environment of application. If plants are being treated in a greenhouse, the formulation can be sprayed by use of a hand sprayer, garden sprayer, fogger or electrostatic sprayer. These methods will distribute an even spray ideally over the entire plant. The electrostatic sprayer is a more preferable method because of the very small electrically charged droplets' attraction to the plant's surfaces but the hand sprayer will also deliver adequate results. Once applied, the formulation can be just left on the plants without taking any other action. However, it is also an option to again treat the plants with a formulation removal step such as a rinse. If a rinse is applied, a clear water rinse may be applied after several days to a week after application. A more preferable rinse would be to use a hypochlorous acid solution of 5 to 10 part per million. The rinse, either plain water or hypochlorous acid, would be a gentle top to bottom application. One skilled in the art of plant management or plant care would find this action congruent with most established practices.

If the environment is an outdoor application, for small scale application, use of a hand sprayer, garden sprayer would be the applicator of choice. A bottom-up followed by a top-down application will ensure coverage of the bottom side of the leaf and the top the leaf and flower. Spot application of the solution to problem areas, such as mold, mildew or insect centers, should receive a direct application. As stated above in the greenhouse application, there is no imperative to rinse the plant but if a rinse is applied a gentle top to the bottom application would appropriate using either plain water or a hypochlorous acid solution of 5 to 10 ppm.

For a large scale, e.g., commercial outdoor application, it is preferred to use a fogger or electrostatic application, ensuring coverage of the under leaf and stalk, flower and leaf surface.

If indoor houseplants were to be treated, a gentle misting of the whole plant using a hand sprayer and the formulation would suffice, such misting covering under the leaf and the leaf surface, including directly apply to any problem areas caused by insects or fungi, if necessary. Again, a rinse could be applied, using either clear water or hypochlorous acid solution of 5 to 10 parts per million.

No matter what the particular plant wash treatment environment, additional rinses following the initial rinse could be practiced as well. The additional rinses could follow the time line from treatment to rinse as the first rinse.

The inventive formula can also include clinoptilolite zeolite, which is a natural zeolite and referred hereinafter as zeolite, as a component part thereof or as a substitute for the diatomaceous earth component. When used either as a substitute for the diatomaceous earth or in combination with the diatomaceous earth, the same weight range of 0.50 to 10.0% by weight would be used. That is the weight range applies to the combination of the zeolite and the diatomaceous or when only one of these components is included in the formulation. When using the two together, a preferred ratio range of the two would be about 1 part of diatomaceous earth to 1 to 3 parts zeolite and a more preferred ratio would be equal parts of diatomaceous earth and zeolite.

While the inventive formulation containing the diatomaceous earth and/or zeolite is disclosed for use as an insecticide/fungicide, the inventive formulation containing the diatomaceous earth and/or zeolite can also be used as a beauty product and skin treatment formulation.

More particularly, the formulation when used as a skin treatment can be used by applying the formulation to a desired part of the skin of the user of the formulation. These skin treatments would include applying the formulation to virtually any part of the skin, e.g., arms, legs, back, hands, face, etc. The formulation is especially effective when used as a face mask, either for a certain period of time, e.g., 20 minutes, or as an overnight mask. After such a skin treatment, the skin is restored and rejuvenated, looking much healthier and polished.

When applying the formulation to the skin of a person, the formulation is used in an effective amount that covers the skin being treated to reduce and remove sebum and exfoliate the skin and soften the appearance of the skin. A typical treatment may use from ¼ ounces to ½ ounces of the formulation.

As such, an invention has been disclosed in terms of preferred embodiments thereof which fulfills each and every one of the objects of the present invention as set forth above and provides a new and improved liquid formulation that can be used as an insecticide/fungicide or plant wash and as a treatment for skin to improve the look and health thereof.

Of course, various changes, modifications and alterations from the teachings of the present invention may be contemplated by those skilled in the art without departing from the intended spirit and scope thereof. It is intended that the present invention only be limited by the terms of the appended claims.

What is claimed is:

1. An aqueous formulation for treatment of one or both of insects and fungi on plants and skin of a person and for plant washing to remove unwanted materials from a surface of the plant, comprises, in weight percent:
   about 0.5 to about 5.0% of one or both of sodium magnesium fluorosilicate (nano) and a bentonite clay;
   about 0.5 to about 10.0% of one or both of a food grade diatomaceous earth and a clinoptilolite zeolite; and
   the balance a HOCl-containing electrolyzed oxygenated aqueous solution having a free available chlorine of 16 to 500 ppm.

2. The aqueous formulation of claim 1, wherein one or both of the sodium magnesium fluorosilicate (nano) and the bentonite clay comprise about 0.75 to about 2.0% and one or both of the food grade diatomaceous earth and the clinoptilolite zeolite comprise about 0.75 to about 5.0%.

3. The aqueous formulation of claim 2, wherein one or both of the sodium magnesium fluorosilicate (nano) comprise about 1.0% and the bentonite clay and one or both of the food grade diatomaceous earth and the clinoptilolite zeolite comprise about 1.0%.

4. The aqueous formulation of claim 1, wherein the free available chlorine of the HOCl-containing electrolyzed oxygenated aqueous solution ranges between 30 and 300 ppm.

5. The aqueous formulation of claim 1, wherein both the diatomaceous earth and the clinoptilolite zeolite are present in the aqueous formulation.

6. The aqueous formulation of claim 5, wherein a ratio of the diatomaceous earth to the clinoptilolite zeolite ranges from about 1:1 to about 1:3.

7. The aqueous formulation of claim 1, wherein either the diatomaceous earth or the clinoptilolite zeolite is present in the aqueous formulation.

8. A method of treating one or more plants for insect and fungal disease control or for plant washing comprising applying an effective amount of the aqueous formulation of claim 1 to the one or more plants to kill at least insects and fungi on the one or more plants or remove unwanted material from plant surfaces to improve plant health.

9. The method of claim 8, wherein the formulation includes both the clinoptilolite zeolite and the diatomaceous earth.

10. The method of claim 8, wherein the formulation includes one of the clinoptilolite zeolite and the diatomaceous earth.

11. A method of treating skin of a person comprising applying an effective amount of the aqueous formulation of claim 1 to the person's skin to improve skin health.

12. The method of claim 11, wherein the formulation includes both the clinoptilolite zeolite and the diatomaceous earth.

13. The method of claim 11, wherein the formulation includes one of the clinoptilolite zeolite and the diatomaceous earth.

* * * * *